United States Patent [19]

Koizumi et al.

[11] Patent Number: 5,589,355
[45] Date of Patent: Dec. 31, 1996

[54] PROCESS FOR PRODUCING RIBOFLAVIN

[75] Inventors: Satoshi Koizumi; Yoshiyuki Yonetani; Sadao Teshiba, all of Machida, Japan

[73] Assignee: Kyowa Hakko Kogyo Co., Ltd., Japan

[21] Appl. No.: 465,795

[22] Filed: Jun. 6, 1995

Related U.S. Application Data

[63] Continuation of Ser. No. 161,394, Dec. 6, 1993, abandoned.

[30] Foreign Application Priority Data

Dec. 7, 1992  [JP]  Japan ................................ 4-326578

[51] Int. Cl.$^6$ .............................. C12P 25/00; C12N 1/21; C12N 15/52; C12N 15/63
[52] U.S. Cl. .................... 435/66; 435/172.3; 435/320.1; 435/252.3; 435/252.32; 435/252.33; 536/23.2
[58] Field of Search .................................. 435/66, 320.1, 435/252.3, 252.33, 172.3; 536/23.2

[56] References Cited

U.S. PATENT DOCUMENTS

| | | | |
|---|---|---|---|
| 4,500,640 | 2/1985 | Katsumata et al. | 435/252.32 |
| 4,617,267 | 10/1986 | Katsumata et al. | 435/91.4 |
| 4,710,471 | 12/1987 | Katsumata et al. | 435/252.32 |
| 5,164,303 | 11/1992 | Heefner et al. | 435/66 |

FOREIGN PATENT DOCUMENTS 63-112996  5/1988  Japan.

OTHER PUBLICATIONS

Clarke et al., (1979) Methods in Enzymology 68:396–408.
Ayala et al., (1980) Modern Genetics, Benjamin/Cummings Publishing Company, Inc. (Menlo Park, CA) pp. 151–154.

Primary Examiner—Robert A. Wax
Assistant Examiner—G. E. Bugaisky
Attorney, Agent, or Firm—Finnegan, Henderson, Farabow, Garrett & Dunner, L.L.P.

[57] ABSTRACT

The present invention provides a process for producing riboflavin efficiently at a low cost, wherein riboflavin is formed and accumulated in a medium by culturing a microorganism carrying a recombinant DNA prepared by inserting into a vector DNA a DNA which is derived from a microorganism belonging to the genus Corynebacterium or Brevibacterium and which, upon introduction into a riboflavin-requiring microorganism, confers on the microorganism the ability to complement its riboflavin requirement.

6 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 5589 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Corynebacterium ammoniagenes ( x i ) SEQUENCE DESCRIPTION: SEQ ID NO:1:

```
GTCGACATTA TGGACGGCCA TTTCGTCCCG AACCTGTCCT TTGGTCCAGA TATCACCAAG      60
GCCGTCGATG GGATCACGGA TCAAACCCTT GATGTGCATT TGATGATCCA GGAGCCAGCA     120
CAGTGGGTAG ACACTTACGC TAAGGCGGTG CAGATTGCAT CATCTTCCAC GTCGAGGCGG     180
TTGAAGACGA GGCAGCAGCG CTTGCATTGG CAGCTAAGAT CCGCGAGCTC GGCGTTCGCG     240
CTGGATTTTC CATTAAGCCC AATACCCCAA TTGAGCCGTG GCTAGATAAG CTGTCCCACT     300
TCGACTTAGT TCTGGTGATG AGTGTTGAAC CGGGCTTTGG CGGGCAGAAA TTTATGCCGG     360
AGATGCTCGA TAAGGTGCGC AAGCTCCGCT CAGCTATCGA TGAGCAAGGC TTAGATACGC     420
TCATCGAAAT TGATGGCGGA ATTTCTGCTG ACACCATCGC GCAAAGCGCG AAGCTGGCT      480
GCGATGCATT CGTGGCGGGT TCGGCAATCT TTAAGCAACG TGACCGCGCA GCCGAGGTAG     540
AGAACCTGCG CGCTTTGGCC ACCGTCTAAT TAAGGGATTA CTGGATTATG GATAGCAACC     600
CCGGTGCAGA CCAAGCCGTG GCTCCGATTG TGGAGCAGGC GTTGCGCACC GCAATGTCTG     660
CAGGGTGGGA AGTGCGCGGG ACTACCAGCC CGAATCCACC GGTGGGTGCG GTAATTATTT     720
CGACTTCGGG TGAGATTGTG GGCACCGGTG CGACTCAGCC GGTGGGCGGG GTGCACGCAG     780
AAGTCCAAGC TCTAGCCGAT GCCGCGGGCA AGACCGAAGG CGCTACCGCC GTGGTGACGC     840
TGGAGCCGTG CCGGCATACC GGCCGCACGG GACCGTGCAC GCAGGCTTTA ATTGAAGCCG     900
GCATCAAAGA TGTCCTTTTC TTACACTCCG ACCCGAATCC CAGTGCGGGC GGCGGGGAAC     960
AGGTGCTTGT CGATGCCGGC ATCAACGTCG TGCAGCTGCC CAGCCCGGAG GGGGTACCGG    1020
ATGCGCTCAT TCCGTGGTTG AAGTCCGTGC AGTTGCGACG TCCCCACGTT ACGTTGAAAT    1080
TTGCGCAAAC TATCGATGGC TTTACTGCAG CTGCCGATGG CACCAGCCAG TGGATCACTG    1140
GGGAAATGGC GCGTGACTAT GTCCACGCTG ACCGTGAACA CCGCGATGCC ATTATCATCG    1200
GCACTGGCAC GGCCTTGATT GATAATCCAT CGCTTACTGC CCGCTATCCA GACGGCACCC    1260
AACGCGAACA CCAACCCCGG CGAGTTGTCA TTGGCCGTCG CAATATTGCG GATGCCGGCG    1320
```

```
ATGCCGCGTC TAATCTCAAC CGGCTTGGAT TTGAGCAATA TGCCACCATC GATGAAGCTC  1380
TGGCCGAGCT TTATGCCACC GGTGCCCGTG ATGTGCTCGT CGAAGGCGGA GCAGGTTTGG  1440
CCTCAGGCTT TGCCAACCAA GGACTGGTGG ATTGGCTGCA GGTCTACCAG GCGCCGCTCC  1500
TACTCGGTGA GGGAATTTCG GTCTTGGCAC ATCCGTTGAC CAATACGTTG AAAGGCGCCA  1560
GCGCGCTTTG CCCGCGGGCA GCTTCTGGCG CTGGGCGATG ATTTATTAAT CAACTACGTG  1620
CGTACTGCAC ACACTAAATA ATTTCACTAA AGGAGAATTG GTTGTTTACT GGGCTGGTTG  1680
AAGAAAAAGG CAAGGTTATC GCGCTGGAGG AGCTTGGGGA TTCTATCCGC ATGCAAATTG  1740
AGGCACCGGT GGTAACCGCT GATGCTCAAC TAGGAGACTC CATTTCTGTC AACGGCGTGT  1800
GCTTGACCGT CGCGGAGCTG GGAGACGCGA CGTTTATCGC CGACATTATG CAGGAATCTC  1860
TAAACCGCTC AGCTTTGGGT GAACTTGCGC CACAGAGCAC GGTAAACCTC GAACGCGCAT  1920
TGCTACCTAC CACCCGATTG GGCGGGCATA TCGTGCAAGG CCATGTCGAT GGCACCGCCA  1980
AACTTATCTC CCGCACTCCG TCGGAGCACT GGGATATTTT GCGTTTCGAA TTGCCTGCGG  2040
ATCTGGCACG TTATGTTGTT GAAAAGGGCT CGATTGCGAT TAGCGGCACG TCTTTGACGG  2100
TATCTGCAAT TGGGGAAGCC TGGTTTGAGG TCTCTTTGAT TCCAGTTACT TTGCGCGACA  2160
CCATCTTGGG TGATTTAGCC GACGGTGATC TGGTTAATCT CGAGGTTGAC GTGTTAGCGA  2220
AGTATGTCGA GAAGATGGTT CGCCCCCAAG GCGAGGTTTA ACAAGGGTAG AGACTAAGCT  2280
AGATAGCTAT GAACGCACCT TTAAATAGCG CAGTTCGTCT GGACTCCATC GAGGAGGCGA  2340
TTGCGGATAT CGCTGCCGGC AAGGCAGTAG TTGTAGTTGA CAACGAGGAC CGTGAGAATG  2400
AGGGTGACCT GATTTTCGCC GCGGAGCTTG CAACACCTGA GCTCGTAGCT TTTATGGTGC  2460
GCTATTCCTC GGGTTATATT TGCGTGCCTT TGCTGCCTGA AGACTGCAAG CGTTTGAACC  2520
TGCCACCGAT GATGGGCAGA AATGAAGACG TGCGCGGTAC TGCGTATACC GTCACGGTTG  2580
ATGCAAATAC AGGCACCACC GGAATCTCCG CCACTAGCCG CGCAGAAACT ATGCTGCGTC  2640
TCGCAGACCC TATGAGCGTG GTGGATGACT TTACCCGTCC AGGGCATGTG GTTCCGCTGG  2700
CTGCACGTCC TAACGGTGTT CTTGAGCGTG ATGGGCACAC GGAAGCCGCC ATCGACTTGG  2760
CTCGCTTGGC GGGCCTGCGT CCAGCGGGTG TTTTGTGTGA AATCGTCTCT GAAGAAGACC  2820
CGACCACGAT GGCTCGTTCC GAAGAGCTGC GTCGTTTTTC TGATGAGCAT GACTTGAAGA  2880
TGATATCCAT CGAGCAGCTC ATCGAATGGC GCCGTCACAA TGAGACTCAG GTACGTCGCA  2940
CGGTCGAAAC CCAGTTGCCG ACGGACTTCG GCTCTTTTAC CGCACTGGGC TACAAGCACG  3000
AGATCGACGG CCAAGAGCAC GTGGCACTGA TTGCAGGTGG CGTGGAAGAA CTCAACGGTG  3060
CCGAGGATGT CTTTGTCCGC GTGCACTCAG AATGCCTCAC CGGCGATGTC TTCCATTCCC  3120
GTCGTTGCGA CTGTGGCCAG CAGCTGCACC AGTCTATGGA GATTATCCAA GAGGCTGGCC  3180
AGGGAATCAT CATTTACTTG CGCGGTCACG AAGGCCGCGG CATTGGACTT TTGGCAAAGC  3240
TTAAGGCCTA CAGCCTGCAA GATTCAGGCC TCGATACTGT CGATGCCAAC CTGGAGCAAG  3300
GCTTGCCGGA AGATGCCCGT GAATACTCAG TCGCCGGGCA AATCCTGCGC GATCTGGGCA  3360
TCAAGTCAGC AAACCTGTTG ACCAATAACC CGCACAAAGG CGAAGGCCTG CGTGGCTTCG  3420
GGGTAGAAGC GTCCGCGCAT ACTCCGGTAG AAATAGAGCC AAACGCAGAC AATATTGATT  3480
ACCTGCGCAC CAAGCGTGAC CGTATGAACC ACGATTTGCC GCAGGTTGCG CGGTGGGACG  3540
CTGCGCACGC GCTGAAGTAA GAACCCTGAA AAACGTCGAA GAAAGCAAGA ACATGAGCAA  3600
AGAAGGACTA CCAGAAGTCG CCACGATTGA TGCCACCGGC ATCTCCGTCG CGGTTATCAG  3660
CGCAACCTGG AACGCAGATA TTTGTGACCG CCTCCATGAG CGAGCACTTG CTCATGCACA  3720
```

| | | | | | |
|---|---|---|---|---|---|
| GCAACTTGGC | GCCGAAGCAG | ATGGTTTCCG | CGTCGTCGGC | GCACTGGAGA | TTCCCGTCGC | 3780
| GGTACAAGAA | GCAGCACGCC | ACTACGACGC | AGTTGTAGCA | CTGGGTTGTG | TCATCCGTGG | 3840
| TGGCACTCCG | CACTTTGATT | ATGTCTGTGA | CTCCGTCACT | CAGGGCCTAA | CCCGAATTGC | 3900
| GCTGGATACT | TCCAAGCCGA | TTGCTAATGG | CGTCTTGACA | GTCAACACCC | ACGACCAAGC | 3960
| GGTGGATCGT | TCAGGTGCAC | CAGGTGCTGC | CGAAGACAAG | GGCGTAGAAG | CCATGCAAGC | 4020
| GGCTTTAGAT | ACTGTGCTGC | AATTGCGTAA | TATCAAAGAA | CGCGCATCAA | AGCGCGGACT | 4080
| GTAGGAGATG | ACTAATTCCA | TGACTGACTC | AACGGCTGGT | GCCCCGGCG | ACTACCAACC | 4140
| GAAGAAGAAG | CTAACTGATG | AAGAGATCTT | GGCGTATACC | ACCGCCGATC | CCTTCGCTAT | 4200
| GACCTCCACG | AAGCCGTGGG | AGTTGACTAT | TTCCTCGCCA | TTTCTGCGCA | AGTGGCGTG | 4260
| GGTGTGCATC | GCGATTGTGA | TTCCCGTGCA | CCTTTTTATG | GGCATCATGC | TGGATGTCGA | 4320
| ATTTACCGGT | GCGTATATCA | CTTTCATCGA | TAAGCTAGCT | TTCCCTGGCA | TCGGTATTGT | 4380
| CATATCGATA | ATCGCGTGGC | TGGCGTTCAA | CCGTCCACGT | CTGCGCGCTA | ATTCTGATGG | 4440
| CGTAGAAATC | CGCAACATCA | TCGGCACGCG | CTTTTACCCG | TGGGAAGTCA | TCTACGGCAT | 4500
| GTCTTTCCCC | GAAGGCTCAC | GCATGGCGCG | CATTGAATTG | CCGAATTTCG | AATACGTGCC | 4560
| AGTCTGGGCA | ATCCAATCCG | GCGATAAAGA | AGCAGCGATT | GCTGCTACCC | GGAACTTCCG | 4620
| CGAACTTGAA | GCGAAGTACA | TGCCGCTGGA | TTAACCAGCA | CAAAGAAGG | GAAGTGGCC | 4680
| ACCGTGGCAG | ATCCAAGCAC | TTACCGGCCT | GCTCCTGGAA | CCATCCCGAC | AGATCCAGGC | 4740
| GTATATAAAT | TCCGCGATGA | AAATAAACGC | GTTGTATATG | TCGGGAAGGC | GAAAAACCTT | 4800
| CGCTCGCGGC | TCTCGAACTA | TTTCCAAGAC | ATCACGCAGC | TGCATCCTCG | CACTCGCCAA | 4860
| ATGGTGCAAA | CCGCGGCGAG | CGTCGAGTGG | ACGGTTGTTG | CCAGCGAAGT | AGAAGCTCTT | 4920
| GCGCTGGAAT | ATACGTGGAT | TAAGAAATTC | GATCCGCGCT | TCAACGTCAA | ATACCGTGAC | 4980
| GATAAAACTT | ATCCGATGCT | GGCGGTATCC | GTTGGCGAGC | GCATTCCGCG | AGCATTTTTC | 5040
| TACCGTGGTC | CGCGCCGTAA | AGGTGTGCGC | TACTTCGGGC | CTTATTCCCA | CGCGTGGGCT | 5100
| GTGCGTGAAG | CCCTGGATCT | ACTCACGCGC | GTCTTTCCCA | TGCGCACGTG | CTCCAAGGGC | 5160
| GTATACAACC | GGCACGAAAG | CCTTGGCCGA | CCGTGTCTTT | TGGGCTATAT | TGGCAAGTGC | 5220
| AATGCACCGT | GTATTGGGCG | AGTGAGCGAG | GACGAGCACC | GCGATACTGT | TAATCAGCTG | 5280
| GTCTCGTTTA | TGAACGGTAA | CACCGGCCCG | GTGGTACGCC | AGCTTACGGC | ACAGATGCAG | 5340
| GAAGCATCGG | AAGCACTAGA | GTTTGAACGC | GCGGCACGCC | TGCGCGATGA | CCTTGAGGCC | 5400
| ATTAATAAAA | TCATGGAGCA | ACAAGCTGTT | GTCTTCACTG | ATTCGACGGA | TGCGGACCTC | 5460
| ATCGCTTTTC | ACACTGATGA | GCTGGAAGCC | GCATTGCAGA | TTTTCCACGT | GCGCGATGGA | 5520
| CGTATCCGCG | GCCAACGCGG | CTGGGTTGTA | GAGCGCATGG | GCGACCAAGC | CCCATTGAAG | 5580
| AAAGTCGAC | | | | | | 5589

( 2 ) INFORMATION FOR SEQ ID NO:2:

( i ) SEQUENCE CHARACTERISTICS:
( A ) LENGTH: 2689 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Corynebacterium ammoniagenes ( x i ) SEQUENCE DESCRIPTION: SEQ ID NO:2:

| | | | | | | |
|---|---|---|---|---|---|---|
| CTGCAGGTCT | ACCAGGCGCC | GCTCCTACTC | GGTGAGGGAA | TTTCGGTCTT | GGCACATCCG | 60 |
| TTGACCAATA | CGTTGAAAGG | CGCCAGCGCG | CTTTGCCCGC | GGGCAGCTTC | TGGCGCTGGG | 120 |
| CGATGATTTA | TTAATCAACT | ACGTGCGTAC | TGCACACACT | AAATAATTTC | ACTAAAGGAG | 180 |
| AATTGGTTGT | TTACTGGGCT | GGTTGAAGAA | AAAGGCAAGG | TTATCGCGCT | GGAGGAGCTT | 240 |
| GGGGATTCTA | TCCGCATGCA | AATTGAGGCA | CCGGTGGTAA | CCGCTGATGC | TCAACTAGGA | 300 |
| GACTCCATTT | CTGTCAACGG | CGTGTGCTTG | ACCGTCGCGG | AGCTGGGAGA | CGCGACGTTT | 360 |
| ATCGCCGACA | TTATGCAGGA | ATCTCTAAAC | CGCTCAGCTT | GGGTGAACT | TGCGCCACAG | 420 |
| AGCACGGTAA | ACCTCGAACG | CGCATTGCTA | CCTACCACCC | GATTGGGCGG | GCATATCGTG | 480 |
| CAAGGCCATG | TCGATGGCAC | CGCCAAACTT | ATCTCCCGCA | CTCCGTCGGA | GCACTGGGAT | 540 |
| ATTTTGCGTT | TCGAATTGCC | TGCGGATCTG | GCACGTTATG | TTGTTGAAAA | GGGCTCGATT | 600 |
| GCGATTAGCG | GCACGTCTTT | GACGGTATCT | GCAATTGGGG | AAGCCTGGTT | TGAGGTCTCT | 660 |
| TTGATTCCAG | TTACTTTGCG | CGACACCATC | TTGGGTGATT | TAGCCGACGG | TGATCTGGTT | 720 |
| AATCTCGAGG | TTGACGTGTT | AGCGAAGTAT | GTCGAGAAGA | TGGTTCGCCC | CCAAGGCGAG | 780 |
| GTTAACAAG | GGTAGAGACT | AAGCTAGATA | GCTATGAACG | CACCTTTAAA | TAGCGCAGTT | 840 |
| CGTCTGGACT | CCATCGAGGA | GGCGATTGCG | GATATCGCTG | CCGGCAAGGC | AGTAGTTGTA | 900 |
| GTTGACAACG | AGGACCGTGA | GAATGAGGGT | GACCTGATTT | TCGCCGCGGA | GCTTGCAACA | 960 |
| CCTGAGCTCG | TAGCTTTTAT | GGTGCGCTAT | TCCTCGGGTT | ATATTTGCGT | GCCTTTGCTG | 1020 |
| CCTGAAGACT | GCAAGCGTTT | GAACCTGCCA | CCGATGATGG | GCAGAAATGA | AGACGTGCGC | 1080 |
| GGTACTGCGT | ATACCGTCAC | GGTTGATGCA | AATACAGGCA | CCACCGGAAT | CTCCGCCACT | 1140 |
| AGCCGCGCAG | AAACTATGCT | GCGTCTCGCA | GACCCTATGA | GCGTGGTGGA | TGACTTTACC | 1200 |
| CGTCCAGGGC | ATGTGGTTCC | GCTGGCTGCA | CGTCCTAACG | GTGTTCTTGA | GCGTGATGGG | 1260 |
| CACACGGAAG | CCGCCATCGA | CTTGGCTCGC | TTGGCGGGCC | TGCGTCCAGC | GGGTGTTTTG | 1320 |
| TGTGAAATCG | TCTCTGAAGA | AGACCCGACC | ACGATGGCTC | GTTCCAAGA | GCTGCGTCGT | 1380 |
| TTTTCTGATG | AGCATGACTT | GAAGATGATA | TCCATCGAGC | AGCTCATCGA | ATGGCGCCGT | 1440 |
| CACAATGAGA | CTCAGGTACG | TCGCACGGTC | GAAACCCAGT | TGCCGACGGA | CTTCGGCTCT | 1500 |
| TTTACCGCAC | TGGGCTACAA | GCACGAGATC | GACGGCCAAG | AGCACGTGGC | ACTGATTGCA | 1560 |
| GGTGGCGTGG | AAGAACTCAA | CGGTGCCGAG | GATGTCTTTG | TCCGCGTGCA | CTCAGAATGC | 1620 |
| CTCACCGGCG | ATGTCTTCCA | TTCCCGTCGT | TGCGACTGTG | GCCAGCAGCT | GCACCAGTCT | 1680 |
| ATGGAGATTA | TCCAAGAGGC | TGGCCAGGGA | ATCATCATTT | ACTTGCGCGG | TCACGAAGGC | 1740 |
| CGCGGCATTG | GACTTTTGGC | AAAGCTTAAG | GCCTACAGCC | TGCAAGATTC | AGGCCTCGAT | 1800 |
| ACTGTCGATG | CCAACCTGGA | GCAAGGCTTG | CCGGAAGATG | CCCGTGAATA | CTCAGTCGCC | 1860 |
| GGGCAAATCC | TGCGCGATCT | GGGCATCAAG | TCAGCAAACC | TGTTGACCAA | TAACCCGCAC | 1920 |
| AAAGGCGAAG | GCCTGCGTGG | CTTCGGGGTA | GAAGCGTCCG | CGCATACTCC | GGTAGAAATA | 1980 |
| GAGCCAAACG | CAGACAATAT | TGATTACCTG | CGCACCAAGC | GTGACCGTAT | GAACCACGAT | 2040 |
| TTGCCGCAGG | TTGCGCGGTG | GGACGCTGCG | CACGCGCTGA | AGTAAGAACC | CTGAAAAACG | 2100 |
| TCGAAGAAAG | CAAGAACATG | AGCAAAGAAG | GACTACCAGA | AGTCGCCACG | ATTGATGCCA | 2160 |
| CCGGCATCTC | CGTCGCGGTT | ATCAGCGCAA | CCTGGAACGC | AGATATTTGT | GACCGCCTCC | 2220 |
| ATGAGCGAGC | ACTTGCTCAT | GCACAGCAAC | TTGGCGCCGA | AGCAGATGGT | TTCCGCGTCG | 2280 |

```
TCGGCGCACT  GGAGATTCCC  GTCGCGGTAC  AAGAAGCAGC  ACGCCACTAC  GACGCAGTTG    2340

TAGCACTGGG  TTGTGTCATC  CGTGGTGGCA  CTCCGCACTT  TGATTATGTC  TGTGACTCCG    2400

TCACTCAGGG  CCTAACCCGA  ATTGCGCTGG  ATACTTCCAA  GCCGATTGCT  AATGGCGTCT    2460

TGACAGTCAA  CACCCACGAC  CAAGCGGTGG  ATCGTTCAGG  TGCACCAGGT  GCTGCCGAAG    2520

ACAAGGGCGT  AGAAGCCATG  CAAGCGGCTT  TAGATACTGT  GCTGCAATTG  CGTAATATCA    2580

AAGAACGCGC  ATCAAAGCGC  GGACTGTAGG  AGATGACTAA  TTCCATGACT  GACTCAACGG    2640

CTGGTGCCCC  CGGCGACTAC  CAACCGAAGA  AGAAGCTAAC  TGATGAAGA                 2689
```

PROCESS FOR PRODUCING RIBOFLAVIN

This application is a continuation of application Ser. No. 08/161,394, filed Dec. 6, 1993, now abandoned.

FIELD OF THE INVENTION

The present invention relates to a process for producing riboflavin (vitamin B2). Riboflavin is an important vitamin which is useful in medicaments, feed additives, coloring agents for food, etc.

BACKGROUND OF THE INVENTION

As the processes for producing riboflavin by fermentation, processes characterized by culturing mutant strains of *Eremothecium ashbyii, Ashbya gossypii, Candida flareri, Saccharomyces cerevisiae*, etc. are known (Progress Industrial Microbiology, 1, 139 (1959), U.S. Pat. No. 5,164,303 and Japanese Published Unexamined Patent Application No.112,996/88).

In addition, European Publication No. 405,370 describes that genetically engineered microorganisms belonging to the genus Bacillus in which Bacillus-derived genes encoding enzymes involved in the biosynthesis of riboflavin are introduced, are used for riboflavin production. The publication contains a description of Bacillus-derived genes encoding enzymes involved in the biosynthesis of riboflavin, but there is no specific description of a DNA which is derived from a microorganism belonging to the genus Corynebacterium or Brevibacterium and which, upon introduction into a riboflavin-requiring microorganism, confers on the microorganism the ability to complement its riboflavin requirement.

SUMMARY OF THE INVENTION

The object of the present invention is to provide a process for producing riboflavin efficiently at a lower cost.

The present invention is directed to a DNA which is derived from a microorganism belonging to the genus Corynebacterium or Brevibacterium and which, upon introduction into a riboflavin-requiring microorganism, confers on the microorganism the ability to complement its riboflavin requirement, a recombinant DNA comprising said DNA and a vector DNA, and a microorganism carrying said recombinant. DNA, as well as to a process for producing riboflavin by culturing said microorganism in a medium until riboflavin is accumulated in the culture, and recovering the riboflavin therefrom.

DETAILED DESCRIPTION OF THE INVENTION

Figure 1:
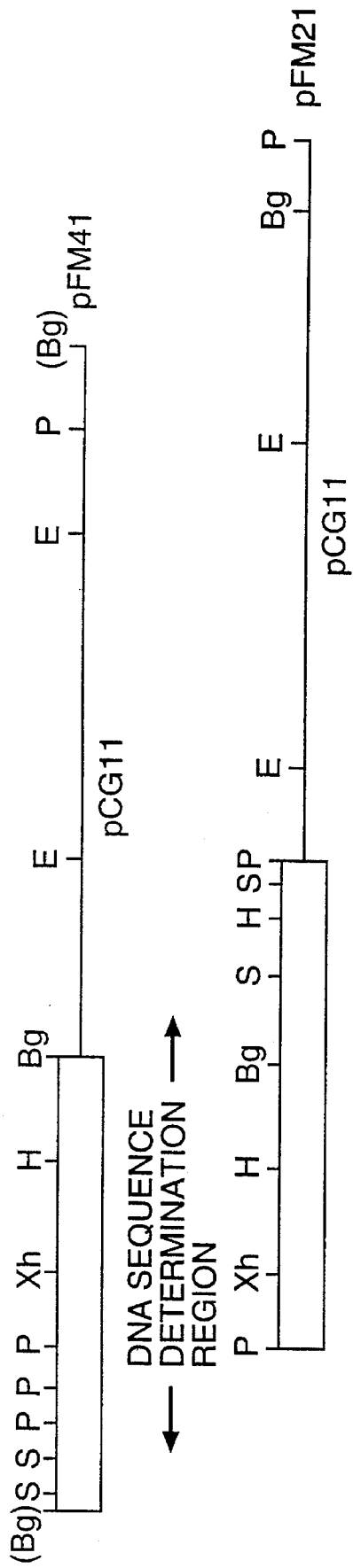
FIG. 1 shows restriction enzyme maps for plasmids pFM21 and pFM41.

As the DNA of the present invention, any DNA is appropriate so long as it is derived from a microorganism belonging to the genus Corynebacterium or Brevibacterium and which, upon introduction into a riboflavin-requiring microorganism, confers on the microorganism the ability to complement, its riboflavin requirement. The DNA is presumed to bear genetic information on enzymes involved in the biosynthesis of riboflavin, because the DNA, upon introduction into a riboflavin-requiring microorganism lacking the enzyme activity involved in the biosynthesis of riboflavin, confers on the microorganism the ability to grow in a riboflavin-free medium.

Specically, the DNA of the present invention is a DNA having the nucleotide sequence set forth in SEQ ID NO:1. Moreover, DNAs having a partial sequence thereof or having a partially replaced sequence by another nucleotide sequence, can be used as the DNA of the present invention as long as it confers on a riboflavin-requiring microorganism the ability to complement its riboflavin requirement. For example, a 2.7 kb DNA fragment having the nucleotide sequence from position 1476 to position 4164 in SEQ ID NO:1 is mentioned. The DNA fragment identified by the sequence from position 1476 to position 4164 in SEQ ID NO:1 is set forth in SEQ ID NO:2. The DNA fragment contains the genes encoding at least two enzymes involved in the biosynthesis of riboflavin, guanosine triphosphate cyclohydrolase and riboflavin synthase.

As the donor source of the DNA of the present invention, a microorganism belonging to the genus Corynebacterium or Brevibacterium, preferably the genus Corynebacterium, is mentioned. Particularly, *Corynebacterium ammoniagenes* KY13313 (Amino acid Nucleic acid, 22, 15 (1970)) is the most preferred.

A chromosomal DNA is obtained from the donor microorganism in a conventional manner, for example by extraction of a chromosomal DNA with phenol [Biochem. Biophys. Acta., 72, 619 (1963)].

As a vector DNA into which the DNA of the present invention is inserted, any of the phage vectors, plasmid vectors, etc., is suitable so long as it is autonomously replicable in a microorganism belonging to the genus Corynebacterium, Brevibacterium or Escherichia. Preferable examples are pCG1, pCG2, pCG4, pCG11, pCE52, pCE53 and pCE54 (U.S. Pat. Nos. 4,617,267, 4,500,640 and 4,710,471).

A recombinant DNA comprising a vector DNA and the DNA which is derived from a microorganism belonging to the genus Corynebacterium or Brevibacterium and which, upon introduction into a riboflavin-requiring microorganism, confers on the microorganism the ability to complement its riboflavin requirement, can be obtained together with a variety of recombinant DNAs by cleaving a donor DNA and a vector DNA with suitable restriction enzymes e.g. PstI and BglII and then ligating both DNAs by the action of DNA ligase. The mixture of ligated DNAs thus obtained is used for transformation of a recipient. Any of the riboflavin-requiring microorganism belonging to the genus Corynebacterium or Brevibacterium and lacking the enzyme activity involved in the biosynthesis of riboflavin can be used as the recipient. For example, *Corynebacterium ammoniagenes* RK122 (Example 4) can be used as the recipient.

The recipient is transformed with the variety of recombinant DNAs thus obtained in a conventional method, such as the protoplast method (Japanese Published Unexamined Patent Application No. 248,394/88), the electroporation method [W. J. Dower et al., Nucleic Acids Research, 16, 6127 (1988)] and the method of Cohen et al. [Proc. Natl. Acad. Sci., U.S.A., 69, 2110 (1979)].

A transformant having the desired enzyme activity involved in the biosynthesis of riboflavin, can be obtained by selecting a transformant capable of growing in a riboflavin-free medium from the transformants thus obtained.

If the vector DNA contains a selective marker e.g. a resistance to an antibiotic, the desired transformant can more easily be selected by addition of the antibiotic to the selective medium.

The desired recombinant DNA can be isolated from the thus selected transformant and then introduced into another microorganism belonging to the genus Corynebacterium or Brevibacterium in a conventional method. Alternatively, the inserted DNA may be excised from the recombinant DNA and ligated to another vector DNA, and then the DNA can be introduced into a microorganism belonging to the genus Corynebacterium or Brevibacterium. Such microorganism includes, for example, *Corynebacterium ammoniagenes,* KY13313, etc.

Using other bacterial host-vector system, the DNA of the present invention can also be introduced into another bacterial species.

Any of known host-vector systems such as those of the genus Escherichia, Bacillus, etc. can be used. Specifically, *Escherichia coli* JM105 [GENE, 33, 103 (1985)] is mentioned for this purpose.

As the transformant having the desired enzyme activity, mention may be made of *Corynebacterium ammoniagenes* KY13313/pFM21 and KY13313/pFM41. KY13313/pFM21 and KY13313/pFM41 carry the recombinant DNAs pFM21 and pFM41, respectively. pFM21 and pFM41 contain the DNA of the present invention. *Corynebacterium ammoniagenes* KY13313/pFM41 has been deposited as *Corynebacterium ammoniagenes* FM41 (FERM BP-4003) with the National Institute of Bioscience and Human-Technology, Agency of Industrial Science and Technology, Japan, as from Sep. 9, 1992, under the Budapest Treaty.

Riboflavin can efficiently be produced at a lower cost by culturing a microorganism belonging to the genus Corynebacterium, Brevibacterium or Escherichia and carrying a recombinant DNA comprising a vector DNA and a DNA which is derived from a microorganism belonging to the genus Corynebacterium or Brevibacterium and which, upon introduction into a riboflavin-requiring microorganism, comfers on the microorganism the ability to complement its riboflavin requirement.

The microorganism is cultured according to a conventional method for culturing of usual microorganisms. That is, the microorganism is cultured under the control of temperature and pH under aerobic conditions in a usual medium containing carbon sources, nitrogen sources, inorganic substances, amino acids, and vitamins.

Any carbon source used may be used so long as the microorganism can assimilate it. For example, carbohydrates such as glucose, fructose, sucrose, molasses, starch, starch hydrolysates etc.; organic acids such as gluconic acid, pyruvic acid, lactic acid, acetic acid etc.; and amino acids such as glycine, glutamic acid, alanine, aspartic acid etc. are mentioned. The carbon source is used preferably in a concentration of 5–40%.

As the nitrogen source, mention may be made of ammonia; various inorganic and organic ammonium salts, such as ammonium chloride, ammonium sulfate, ammonium phosphate, ammonium nitrate, ammonium carbonate, ammonium acetate etc.; nitrogen-containing organic substance, such as urea, peptone, NZ amine, meat extract, yeast extract, corn steep liquor, casein hydrolysates, fish meal or its digested product; and various amino acid, such as glycine, glutamic acid etc. These substances are employed usually in a concentration of 0.1–10%.

As the inorganic compound, mention may be made of potassium dihydrogen phosphate, dipotassium hydrogen phosphate, magnesium sulfate, magnesium phosphate, sodium chloride, ferrous sulfate, manganese sulfate, zinc sulfate, calcium carbonate, etc. If required by the microorganisms for their growth, nutrients such as amino acids, nucleic acids, vitamins, etc., are added in a suitable amount. Where these substances are contained in other nutrients as enumerated above, their addition is not particularly required.

Culturing is carried out under aerobic conditions, for example by shaking culture or by aeration-stirring culture, preferably at 20°–40° C. for 24–144 hours. The pH of the medium is preferably maintained around neutrality by addition of aqueous ammonia, a urea solution, a sodium hydroxide solution, etc.

The riboflavin thus formed can be quantitatively determined by high performance liquid chromatography using a reverse phase column [e.g., RP-18 (a product of Merck)] with its fluorescence intensity monitored at an emission wavelength of 530 nm and an excitation wavelength of 450 nm.

Riboflavin can be recovered from the culture by a conventional purification means such as precipitation, chromatography e.g. by use of an ion-exchange resin, etc.

According to the present invention, riboflavin can be efficiently produced by fermentation.

EXAMPLES

Hereinafter, the present invention is specifically described with reference to the following examples.

EXAMPLE 1

Preparation of Chromosomal DNA

*Corynebacterium ammoniagenes* KY13313 was inoculated into an AIII AG medium [10 g/l polypeptone, 10 g/l meat extract, 5 /l yeast extract, 3 g/l sodium chloride, 30 µg/l biotin, 20 mg/l adenine and 10 g/l glycine, pH 7.2] and cultured by shaking at 30° C. for 10 hours. 0.6 g of the cultured cells was suspended in 18 ml of P-4 buffer [25 mM N-tris(hydroxymethyl)methyl-2-aminoethasulfonic acid, (pH 7.6), 70 mM sodium chloride, 5 mM magnesium chloride, 5 mM calcium chloride and 1.6 M D-sorbitol], followed by addition of 2 ml of P-4 buffer containing 12 mg/ml lysozyme and 3 mg/ml acromopeptidase. The cell suspension was allowed to stand at 30° C. for 20 hours, thus giving a protoplast. The protoplast was collected by centrifugation, then suspended in TSMC buffer [50 mM Tris-HCl buffer (pH 7.5), 0.6M sodium succinate, 10 mM magnesium chloride and 10 mM calcium chloride] and centrifuged again. The protoplast obtained as a precipitate was suspended in 12 ml of TES buffer [10 mM Tris-HCl buffer (pH 8.0), 1 mM disodium ethylenediaminetetraacetate (EDTA) and 10 mM sodium chloride] and allowed to stand at 4° C. for 30 minutes. 0.28 ml of 5M sodium chloride and 0.04 ml of 5 mg/ml ribonuclease A (product of Sigma) were added thereto, and the mixture was allowed to stand at 37° C. for 20 minutes. Subsequently, 0.72 ml of 10% sodium lauryl sulfate was added thereto, and the mixture was allowed to stand at 4° C. for 2 hours and then heated at 65° C. for 5 minutes. To the solution was added 13 ml of phenol saturated with TES buffer, and the mixture was thoroughly stirred. The solution was centrifuged and the aqueous layer was recovered. This procedure of extraction with phenol was repeated further 2 times, and then an equal volume of chloroform was added, thoroughly stirred, and centrifuged, thus giving an aqueous layer. 1.2 ml of 2.5M sodium acetate was added to 12 ml of the solution thus obtained, followed by addition of 30 ml of ethanol. The chromosomal DNA thus precipitated was wound around a glass rod and then dried. The product was dissolved in 1 ml of TE buffer [10 mM Tris-HCl (pH 8.0) and one mM EDTA].

EXAMPLE 2

Preparation of Recombinant DNA 40 units of restriction enzyme PstI (product of Takara Shuzo Co., Ltd.) was added to a solution containing 50 µg of the chromosomal DNA obtained in Example 1 and the mixture was allowed to stand at 37° C. for 3 hours. Separately, 40 units of restriction enzyme PstI was added to a solution containing 50 µg of vector pCG11 DNA as constructed according to the method as described in U.S. Pat. No. 4,500,640, and the mixture was allowed to stand at 37° C. for 3 hours, followed by addition of 5 units of alkaline phosphatase. The mixture was dephosphorylated at 65° C. for 1 hour. From the above two reaction solutions, chromosomal DNA and vector DNA were purified by phenol extraction and ethanol precipitation in the same manner as described above. For preparation of recombinant DNAs, 10 µg of chromosomal DNA and 20 µg of vector DNA thus treated were ligated at 16° C. for 16 hours in the presence of 700 units of T4 DNA ligase (product of Takara Shuzo Co., Ltd. ) in a T4 ligase buffer [66 mM Tris-HCl buffer (pH 7.6), 6.6 mM magnesium chloride, 10 mM dithiothreitol and 0.1 mM ATP].

40 units of restriction enzyme BglII (product of Takara Shuzo Co., Ltd.) was added to a solution containing 50 µg of the above chromosomal DNA, and the DNA was digested at 37° C. for 3 hours in the same manner as described above. Separately, 40 units of restriction enzyme BglII was added to a solution containing 50 µg of the vector pCG11 DNA, and then the vector was digested at 37° C. for 3 hours. After addition of 5 units of alkaline phosphatase, the mixture was dephosphorylated at 65° C. for one hour. From the resulting two reaction solutions chromosomal DNA and vector DNA were purified by phenol extraction and ethanol precipitation in the same manner as described above. For preparation of recombinant DNAs, 10 µg of chromosomal DNA and 20 µg of vector DNA thus treated were ligated at 16° C. for 16 hours in the presence of 700 units of T4 DNA ligase (product of Takara Shuzo Co., Ltd.) in the T4 ligase buffer.

EXAMPLE 3

Acquisition of a Riboflavin-requiring Strain From *Corynebacterium ammoniagenes*

Riboflavin-requiring strain RK122 was obtained from *Corynebacterium ammoniagenes* KY13313 in the following manner.

*Corynebacterium ammoniagenes* KY13313 was cultured at 30° C. for 7 hours in a medium having the same composition as AIII AG medium except that glycine is not contained, and then mutated at 30° C. for 90 min. with 100 µg/ml N-methyl-N'-nitro-nitrosoguanidine. The cells were collected, washed, and inoculated into a riboflavin-free minimum liquid medium [20 g/l glucose, 0.1 g/l $KH_2PO_4$, 0.3 g/l $K_2HPO_4$, 0.3 g/l $MgSO_4 \cdot 7H_2O$), 0.01 g/l $CaCl_2 \cdot 2H_2O$, 10 mg/l $FeSO_4 \cdot 7H_2O$, 1 mg/l $ZnSO_4 \cdot 7H_2O$, 4 mg/l $MnSO_4 \cdot 4-6H_2O$, 0.2 mg/l $CuSO_4 \cdot 5H_2O$, 40 mg/l L-cystein, 10 mg/l vitamin $B_1$, 20 mg/l Ca-D-pantothenic acid, 60 µg/l biotin, 3 g/l $NH_4Cl$, 2 g/l urea, 50 mg/l adenine, pH 7.2], followed by culturing at 30° C. 100 U/ml penicillin G was added at the logarithmic growth phase, followed by additional 16-hour culturing at 30° C. so that the riboflavin-requiring strains were concentrated. Riboflavin-requiring strain RK122 capable of growing only in a riboflavin-containing minimum medium was obtained by replica plating on a minimum agar medium or without 5 mg/l riboflavin [a minimum liquid medium containing 2% agar].

EXAMPLE 4

Transformation of the Riboflavin-requiring Strain *Corynebacterium ammoniagenes* RKIZZ with the Recombinant DNA According to the electroporation method [W. J. Dower et al., Nucleic Acids Research, 16, 6127 (1988)], the riboflavin-requiring strain was transformed with the recombinant DNA in the following manner.

*Corynebacterium ammoniagenes* RK122 was cultured at 30° C. for 5 hours in an AIII AG medium, then washed with 15% glycerol solution (cooled on ice) containing 272 mM sucrose, and suspended in the same solution as mentioned above. The resulting cell suspension was mixed with a solution of the PstI-digested recombinant DNA obtained in Example 2, and transformation was carried out with a gene pulser (Bio-Rad Laboratories, Richmond, Calif., U.S.A.) according to the electroporation method (a voltage of 2.5 kV, capacity of 25 µF, and resistance of 200 Ω).

Then, the cell suspension was placed onto a minimum agar medium containing 150 µg/l spectinomycin, and cultured at 30° C. for 3 days. *Corynebacterium ammoniagenes* RK122/pFM21 (being resistant to spectinomycin and requiring no riboflavin) was isolated from colonies occurring on the agar plate medium.

According to the method as described above, transformant RK122/pFM41 was obtained using the BglII-digested recombinant DNA obtained in Example 2.

EXAMPLE 5

Extraction of Plasmids From the Transformants

The transformants RK122/pFM21 and RK122/pFM41 were cultured respectively in 250 ml of AIII AG medium containing spectinomycin. According to the method as described in Example 2, plasmid DNAs, each about 100 µg, were obtained respectively from the culture of RK122/pFM21 and RK122/pFM41, and these plasmids were designated pFM21 and pFM41, respectively. FIG. 1 shows restriction enzyme maps for the recombinant plasmids pFM21 and pFM41 where the inserted fragments are 4.7 and 4.2 kb, respectively. In pFM41 set forth in FIG. 1, the BglII site in the parenthesis could not be cleaved with BglII owing to some possible reasons such as microorganism upon the cleavage of the chromosomal DNA or the treatment of the vector DNA with phosphatase. The 2.7 kb fragment (SEQ ID NO:2), excised with restriction enzymes PstI and BglII, was contained in both plasmids.

EXAMPLE 6

Measurement of Riboflavin Synthase Activity

According to the method as described in Method in Enzymology 122,192 (1986), the transformants KY13313/pCGll, KY13313/pFM21, and KY13313/pFM41 were measured for their riboflavin synthase activity. The result indicated that the transformants carrying recombinant DNAs pFM21 and pFM41 had enzyme activities 3.8 and 1.8 times respectively as high as that of the transformant carrying the vector pCG11 only.

EXAMPLE 7

Measurement of Guanosine Triphosphate Cyclohydrolase Activity

According to the method as described in Archives of Microbiology, 124, 255 (1980), the transformants KY13313/pCG11, KY13313/pFM21 and KY13313/pFM41 were measured for their guanosine triphosphate cyclohydrolase activity. The result indicated that the transformants carrying pFM21 and pFM41 exhibited 6.1- and 4.3-fold high enzyme activities respectively as compared with that of the transformant carrying the vector pCG11 only.

EXAMPLE 8

Analysis of the DNA Capable of Conferring on the Riboflavin-requiring Strain the Ability to Complement Its Riboflavin Requirement The 5.6 kb SalI-SalI fragment (containing the 2.7 kb fragment (SEQ ID NO:2) in common) inserted into plasmid pFM21 and pFM41 was determined for its DNA nucleotide sequence by the dideoxy method [Messing, J., Method in Enzymology, 101, 20 (1983)]. The result is set out SEQ ID NO:1.

EXAMPLE 9

Introduction of the Plasmid into *Escherichia coli*

A solution containing 1 µg of plasmid pFM21DNA obtained in Example 5 was digested at 37° C. for 1 hour with 2 units of restriction enzyme PstI. Then, a 4.7 kb fragment was isolated from the digested product by agarose gel electrophoresis. Separately, 0.5 µg of vector pUC19 (product of Takara Shuzo Co., Ltd.) was digested at 37° C. for 1 hour with 2 units of PstI and then dephosphorylated with alkaline phosphatase in the same manner as described in Example 2. The vector DNA thus obtained was then subjected to phenol extraction and ethanol precipitation. The above pFM21-derived DNA fragment, 100 ng, was mixed with 50 ng of the above vector DNA. The mixture was ligated at 16° C. for 2 hours in the presence of 100 units of T4 ligase in the T4 ligase buffer. The resulting recombinant DNA was used for transformation of *E. coli* JM105 according to the method as described by Cohen et al. [Proc. Natl. Acad. Sci., U.S.A., 69, 2110 (1979)], and the cells were plated on an LB agar medium [a medium prepared by adding 1.5% agar to an LB liquid medium (10 g/l bactotrypton, 5 g/l yeast extract, 5 g/l sodium chloride, pH 7.2)) containing 100 mg/l of ampicillin, 0.1 mM isopropylthiogalactoside and 0.004% of 5-bromo-4-chloro-3-indoyl-β-D-galactopyranoside.

From the resulting white transformant, plasmid DNA was isolated and purified according to the method of Maniatis et al. [Molecular Cloning A Laboratory Manual, Cold Spring Harbor Laboratory (1982)]. This plasmid DNA was analyzed for its structure by a digestion with various restriction enzymes. As a result, the plasmid DNA was found to have the structure set forth in FIG. 2 where a pFM21-derived DNA fragment containing the genes encoding the enzymes involved in the synthesis of riboflavin has been inserted downstream of pUC19 lac promoter, and this plasmid DNA was designated pFM201.

EXAMPLE 10

Production of Riboflavin By Use of An *Escherichia coli* Transformant

A transformant, *Escherichia coli* JM105/pFM201 obtained in Example 9 was inoculated into 8 ml of LB liquid medium containing 100 mg/l ampicillin, followed by culturing at 30° C. for 16 hours. The culture solution thus obtained was inoculated into 8 ml of minimal medium containing 100 mg/l ampicillin (3 g/l $KH_2PO_4$, 5 g/l NaCl, 1 g/l $NH_4Cl$, 6 g/l $NaHPO_4$, 0.25 g/l $MgSo_4 \cdot 7H_2O$, 4 mg/l vitamin $B_1$ and 3 g/l glucose) and cultured at 30° C. for 24 hours. The amount of riboflavin accumulated in the culture solution was 14.4 mg/l. In contrast, 0.3 mg/l of riboflavin was accumulated in the culture obtained under the same conditions with respect of *E. coli* JM105/pUC19 carrying only the vector plasmid pUC19.

EXAMPLE 11

Production of Riboflavin By Use of a *Corynebacterium ammoniagenes* Transformant

*Corynebacterium ammoniagenes* KY13313 was transformed in the method described in Example 4 with the pFM41DNA obtained in Example 5. A suspension of the cells was plated on a medium containing 150 µg/ml of spectinomycin and cultured at 30° C. for 3 days. A spectinomycin-resistant transformant, *Corynebacterium ammoniagenes* FM41 (FERM BP-4003), was obtained from the growing colonies.

*Corynebacterium ammoniagenes* FM41 was inoculated into 8 ml of seed medium [10 g/l polypeptone, 10 g/l meat extract, 5 g/l yeast extract, 3 g/l sodium chloride, 30 µg/l biotin, 20 mg/l adenine and 150 mg/l spectinomycin, pH 7.2] in a test tube. The cells were then cultured at 30° C. for 24 days by shaking. 1.5 ml of the culture was inoculated into 30 ml of fermentation medium (Table 1) put in a 300 ml Erlenmeyer flask. After 72 hours of shaking culture at 30° C., riboflavin was accumulated in an amount of 620 mg/l in the culture. In contrast, riboflavin was accumulated in an amount of 35 mg/l in the culture obtained under the same conditions with respect of *Corynebacterium ammoniagenes* KY13313 carrying only the vector plasmid pCG11.

TABLE 1

| component | content |
|---|---|
| polypeptone | 10 g/l |
| glucose | 80 g/l |
| $KH_2PO_4$ | 1 g/l |
| $K_2HPO_4$ | 3 g/l |
| $MgSO_4 \cdot 7H_2O$ | 1 g/l |
| $CaCl_2 \cdot 2H_2O$ | 0.1 g/l |
| $FeSO_4 \cdot 7H_2O$ | 10 mg/l |
| $ZnSO_4 \cdot 7H_2O$ | 1 mg/l |
| $MnSO_4 \cdot 4-6H_2O$ | 4 mg/l |
| $CuSO_4 \cdot 5H_2O$ | 0.2 mg/l |
| L-cysteine | 40 mg/l |
| vitamin $B_1$ | 10 mg/l |
| Ca-D-pantothenic acid | 20 mg/l |
| biotin | 60 µg/l |
| $(NH_4)_2SO_4$ | 5 g/l |
| urea | 5 g/l |
| adenine | 100 mg/l |
| spectinomycin | 150 mg/l |
| $CaCO_3$ | 20 mg/l |
| pH 7.2 | |

EXAMPLE 12

Difference From Bacillus-derived Gene 5 units of restriction enzyme PstI was added to a solution containing 2 μg of chromosomal DNA from *Bacillus subtilis* 168, and the DNA was digested for 5 hours at 37° C. Subsequently, the DNA fragments were subjected to agarose gel electrophoresis, immobilized onto a nylon filter, and subjected to Southern hybridization with a 1 kb XhoI-HindIII fragment as a probe derived from pFM201, using a non-radioiso system DNA labeling and detection kit produced by Boehringer Mannheim Yamanouchi Co., Ltd. As a result, no hybridization was observed between the probe and the chromosomal DNA from the strain 168.

---

What is claimed is:

1. An isolated DNA fragment which comprises a DNA having the nucleotide sequence set forth in SEQ ID NO:2.

2. A recombinant DNA comprising the isolated DNA fragment as claimed in claim 1 and a cloning vector DNA.

3. A microorganism belonging to the genus Brevibacterium, Corynebacterium or Escherichia and carrying the recombinant DNA as defined in claim 2.

4. A biologically pure culture of *Corynebacterium ammoniagenes* FERM BP-4003.

Figure 2:
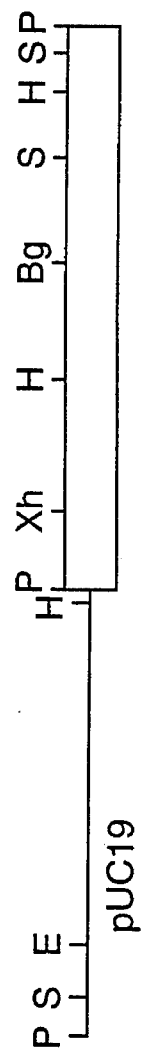
FIG. 2 shows a restriction enzyme map for plasmid pFM201.

5. A recombinant DNA as claimed in claim 2 selected from the group consisting of pFM41, PFM21 and pFM201 as illustrated in FIGS. 1 and 2.

6. A process for producing riboflavin, which comprises culturing in a medium the microorganism as defined in claim 3 until riboflavin is accumulated in the culture, and recovering the riboflavin therefrom.

* * * * *